(12) United States Patent
    Yamazaki (10) Patent No.: US 9,649,634 B2
(45) Date of Patent: May 16, 2017

(54) INTERCONNECTION MECHANISM FOR COLUMN AND NEEDLE

(71) Applicant: SHIMADZU CORPORATION, Kyoto-shi, Kyoto (JP)

(72) Inventor: Tomoyuki Yamazaki, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/993,540

(22) Filed: Jan. 12, 2016

(65) Prior Publication Data

US 2016/0209376 A1    Jul. 21, 2016

(30) Foreign Application Priority Data

Jan. 19, 2015    (JP) ................... 2015-007351

(51) Int. Cl.
    *B01L 99/00*    (2010.01)
    *B01L 3/00*     (2006.01)
    *G01N 30/18*    (2006.01)
    *G01N 30/20*    (2006.01)

(52) U.S. Cl.
    CPC ............ *B01L 3/563* (2013.01); *G01N 30/18* (2013.01); *B01L 2200/026* (2013.01); *B01L 2200/0631* (2013.01); *B01L 2200/0689* (2013.01); *B01L 2300/0832* (2013.01); *G01N 2030/201* (2013.01); *G01N 2030/202* (2013.01)

(58) Field of Classification Search
    CPC .................. G01F 17/00; G01N 1/10
    See application file for complete search history.

(56) References Cited

U.S. PATENT DOCUMENTS

2002/0007671 A1*    1/2002    Lavi ............... A61M 5/19
                                                73/149

FOREIGN PATENT DOCUMENTS

JP    2-122260 A       5/1990
JP    2003-149217 A    5/2003

\* cited by examiner

*Primary Examiner* — Jyoti Nagpaul
(74) *Attorney, Agent, or Firm* — Westerman, Hattori, Daniels & Adrian, LLP (57) ABSTRACT

Provided is a mechanism for connecting columns and needles, including: a base member 60 on which needles 61*a* and 61*b* with their tips directed upward are provided; and a column rack 10 having column holders for holding columns 10*a* and 10*b* in an upright position while allowing all upward shift of the columns, with an opening provided below each column holder. With the needles 61*a* and 61*b* positioned directly below the openings, the base member 60 is elevated until its upper surface comes in contact with the bottom of the column rack 10, whereby the needles 61*a* and 61*b* are inserted through the openings into the columns 20*a* and 20*b*. When the base member 60 is in contact with the column rack 10, the columns 20*a* and 20*b* are pushed by the needles 61*a* and 61*b* to a higher position within the column rack 10 than their original position.

4 Claims, 5 Drawing Sheets

CONVENTIONAL EXAMPLE

Fig. 7B

PRESENT EMBODIMENT

Fig. 8

INTERCONNECTION MECHANISM FOR COLUMN AND NEEDLE

TECHNICAL FIELD

The present invention relates to a system for separating or purifying a target component by means of a column, and more specifically, to a mechanism for connecting a needle in a passage for liquid to that column.

BACKGROUND ART

In pharmaceuticals and similar fields, preparative separation-purification systems employing liquid chromatographs are used in order to collect samples of various lands of chemically synthesized compounds which are to be stored in a library or subjected to detailed analyses. For example, the systems disclosed in Patent Documents 1 and 2 have been conventionally known as this type of preparative separation-purification system.

In a preparative separation-purification system, target components (compounds) in a sample solution are temporally separated by a liquid chromatograph. The separated target components are individually introduced into separate trap columns and temporarily captured in those columns. Subsequently, a solvent ("eluting solvent") is passed through each tap column to quickly elute the component captured in the trap column. Consequently, a plurality of solutions, each of which contains one target component at a high level of concentration, are collected in separate containers ("collection containers"). These separately collected solutions are subjected to a vaporizing and drying process to remove the solvent and collect the target components in solid forms.

Before and after the aforementioned process of eluting the target component from the trap column (which is hereinafter called the "eluting treatment"), the "pretreatment" and "posttreatment" phases are respectively performed. In the pretreatment phase, a predetermined kind of pretreatment liquid (which is selected according to the kind of target component) is passed through the trap column before the eluting treatment in order to wash away components other than the target component present in the trap column ("contaminants"). In the posttreatment phase, the trap column which has undergone the eluting treatment is rinsed with a predetermined kind of posttreatment liquid in order to make it ready for reuse.

In such a preparative separation-purification system, a needle having an internal passage for a liquid is used to pass the pretreatment liquid, eluting solvent and posttreatment liquid through the trap column. The needle has a tip portion which is tapered toward the tip and a base end to which a flexible tube made of a resin or similar material is connected. On the other hand, the trap column has a needle port made of a resin or similar material at its inlet end. By holding the trap column in an upright position with the inlet end directed downward and inserting the tip of the needle into the needle port of the column from below, the tube can be connected to the tap column. The needle port has a vertically penetrating passage formed inside. At the lower (inlet) end of tins passage, a funnel-like portion whose diameter decreases upward is formed. As noted earlier, the tip portion of the needle is tapered. Therefore, when the needle which has been inserted into the passage of the needle port from below reaches a certain height during its upward motion, the outer circumferential surface of the tip portion of the needle comes in close contact with the inner circumferential surface of the funnel-like portion of the passage, whereby a liquid-tight connection is seemed.

CITATION LIST

Patent Literature

Patent Literature 1: JP 2-122260 A
Patent Literature 2: JP 2003-149217 A

SUMMARY OF INVENTION

Technical Problem

In the connecting operation, if the elevation distance of the needle is insufficient, the sealing efficiency at the connection between the needle and the column becomes insufficient Conversely, if the elevation distance of the needle is too large, the connection undergoes an excessive amount of load. Therefore, in the previously described process of inserting the needle into the needle port provided at the inlet end (lower end) of the column, it is necessary to precisely control the motion of the needle. However, since the individual columns, needles and needle ports have slight differences in their dimensions, it has been difficult to control the elevation distance of the needle so as to always obtain a sufficient level of sealing efficiency at the connection while preventing the excessive amount of load.

Normally, in a preparative separation-purification system, a plurality of trap columns with different kinds of tar get components respectively captured and a plurality of collection containers for separately collecting those target components can be set within the system. The sequence process of the pretreatment elating treatment and posttreatment phases is performed far each trap column. According to this method, the treatment process for the next trap column cannot be initiated until the sequence of treatments for one tap column is completed. Therefore, a considerable amount of time is required until the treatments for all trap columns are completed.

One possible method for solving this problem is to perform a portion or the entirety of the aforementioned sequence of phases (i.e. the pretreatment, eluting treatment and posttreatment phases) simultaneously for two or more columns (in a temporally overlapped manner). For this operation, the system needs to have two or more needles for introducing a liquid into the trap columns.

In the case of providing two or more liquid-introducing needles, it is preferable to provide those needles next to each other on a common base member so as to drive them with a common mechanism and thereby simplify the system configuration. In this case, if the plurality of trap columns with their inlet ends directed downward are arranged at intervals corresponding to those of the needles, it is possible to simultaneously connect or disconnect the needles to or from the inlet ends of the trap columns by elevating or lowering the base member.

However, if this configuration is adopted, even an extremely small difference in the vertical position of the tips of the needles or that of the inlet ends of the trap columns makes it impossible to obtain the same level of sealing efficiency at all of the connections between the needles and the trap columns, which may possibly cause the liquid to leak from some of the connections or create an excessive amount of load at some of the connections.

Those problems are not limited to the previously described preparative separation-purification system but are common to any systems having the mechanism of connecting a column to a liquid passage through a needle.

The present invention has been developed in view of the previously described points. The first problem to be solved is to provide an interconnection mechanism for a column and a needle in which the column and the needle can be securely connected without creating an excessive amount of load at the connection even if there is an error in the dimensions of the column and/or needle. The second problem is to provide an interconnection mechanism for a column and a needle which allows for multiple connections of the needles and columns and yet can achieve the same level of sealing efficiency at all of the connections.

Solution to Problem

An interconnection mechanism for a column and a needle according to the first aspect of the present invention developed for solving the previously described problems includes:

a) a needle having an internal passage through winch a liquid is to be passed and a rear end to which a tube for supplying the liquid is to be connected;

b) a column rack having a column holder for holding the column in an upright position while allowing an upward shift of the column and an opening provided below the column holder; and c) a moving system for inserting the needle into the lower end of the column through the opening by changing the vertical position of the needle and/or the column rack by a predetermined distance, with the needle positioned directly below the opening and the tip of fee needle directed upward, wherein:

when the vertical position of the needle and/or the column rack is changed by the predetermined distance by the moving system, the column in which the needle is inserted is pushed upward by the needle and thereby shifted to a higher position within the column rack than the position at which the column is located before the insertion of the needle.

In one mode of the interconnection mechanism for a column and a needle according to the first aspect of the present invention, a needle port is prowled at the lower end of the column, the needle port having an internally formed port-inside passage, with a seal portion formed on the inner circumferential surface of the port-inside passage, the seal portion configured to come in contact with the outer circumferential surface of a tip portion of the needle and thereby create a liquid-tight connection between the needle and the column; and within the column holder, the vertical distance from the upper end of the column rack to the seal portion before the insertion of the needle is greater than the vertical distance from the upper end of the column rack to the tip of the needle when the needle is inserted into the lower end of the column by the moving system and the outer circumferential surface of the tip portion of the needle is thereby made to be in contact with the seal portion.

An interconnection mechanism for a column and a needle according to the second aspect of the present invention developed for solving the previously described problems includes:

a) a plurality of needles, each of the needles having an internal passage through which a liquid is to be passed and a rear end to which a tube for supplying the liquid is to be connected;

b) a base member on which the plurality of needles are provided, with the tips of the needles directed upward;

c) a column rack having a plurality of column holders for respectively holding a plurality of columns in an upright position while allowing an upward shift of the columns, and a plurality of openings respectively provided below the plurality of column holders; and d) a moving system for inserting the needles info the lower ends of the columns through the respective openings by changing the vertical position of the base member and/or the column rack with the needles positioned directly below the respective openings so as to bring the base member and the column rack to a predetermined distance from each other, wherein:

when the column rack and the base member are positioned at the predetermined distance from each other by the moving system, each of the columns in which one of the needles is inserted is pushed upward by the needle and thereby shifted to a higher position within the column rack than the position at which the column is located before the insertion of the needle.

In one mode of the interconnection mechanism, for a column and a needle according to the second aspect of the present invention, a needle port is provided at the lower end of each of the columns, the needle port having an internally formed port-inside passage, with a seal portion formed on the inner circumferential surface of the port-inside passage, the seal portion configured to come in contact with the outer circumferential surface of a tip portion of the needle and thereby create a liquid-tight connection between the needle and the column; and within each of the column holders, the vertical distance from the upper end of the column rack to the seal portion before the insertion of the needle is greater than the vertical distance from the upper end of the column rack to the tip of the needle when the column rack and the base member are positioned at the predetermined distance from each other by the moving system.

Advantageous Effects of the Invention

In the interconnection mechanism for a column and a needle according to the first or second aspect of the present invention having the previously described configuration, when the needle is inserted into the column, the column is pushed upward by the needle. In this state, due to its own weight, the column is pressed against the tip of the needle, whereby the tip of the needle is held in close contact with the inlet end of the column. By this mechanism, the needle and the column can be securely connected together without creating an excessive amount of load at the connection of the two elements even if there is an error in the dimensions of the needle and/or the column.

Additionally, in the second aspect of the present invention, since each of the columns on the column rack can be independently shifted, an equal degree of sealing efficiency can be obtained at all of the connections between the needles and the columns even if there is a difference in the vertical position of the tips of the needles or that of the inlet ends of the columns. Accordingly, a plurality of columns can be concurrently treated without causing a leakage of liquid or creating an excessive amount of load at any of the connections between the needles and the columns.

BRIEF DESCRIPTION OF DRAWINGS

FIGS. 7A and 7B are time charts showing the treatments performed on two hap columns, where

DESCRIPTION OF EMBODIMENTS

Figure 1:
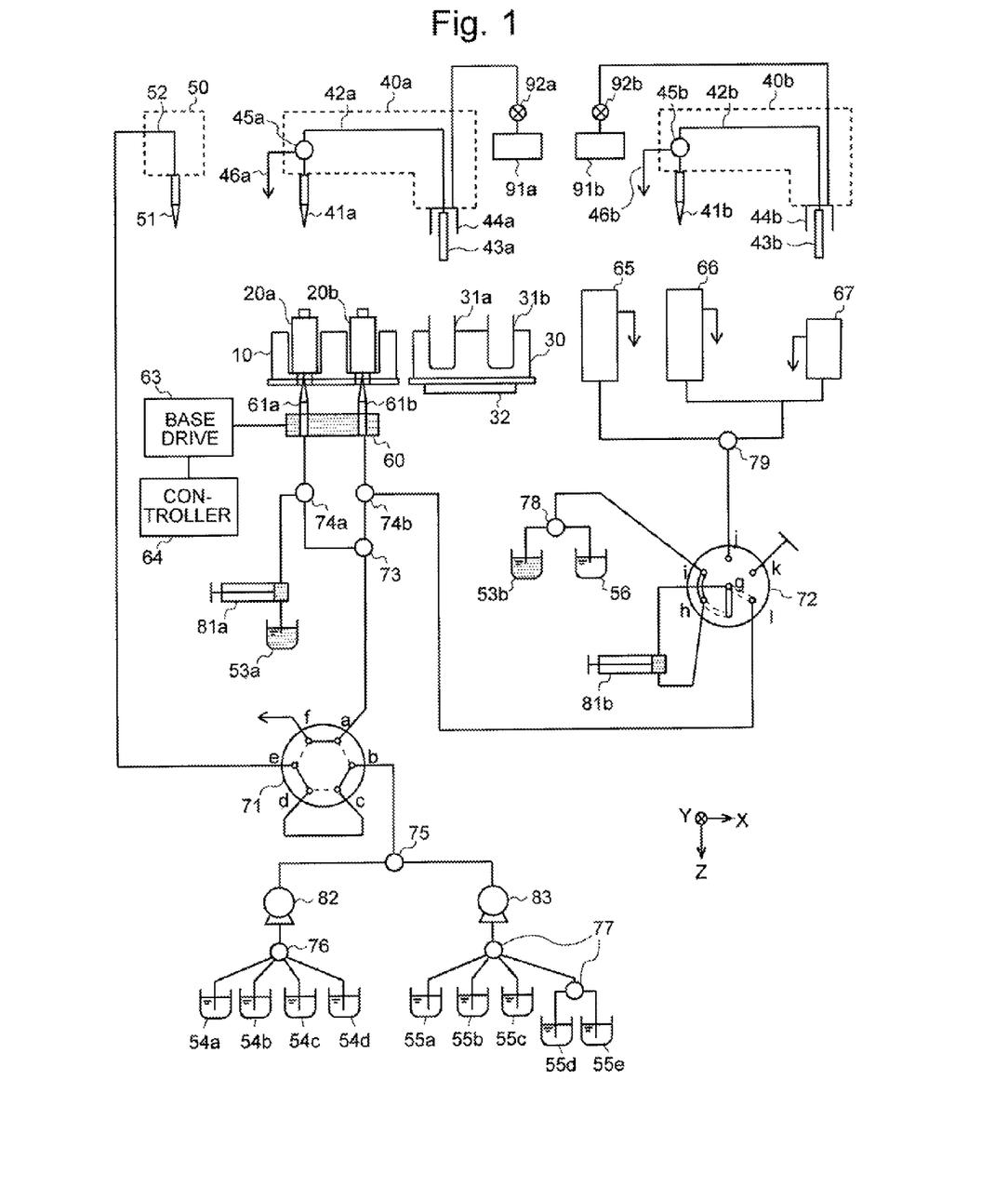
FIG. 1 is a schematic configuration diagram of a collecting and powdering system having a connection mechanism according to one embodiment of the present invention.

Specific modes for carrying out the present invention are hereinafter described by means of embodiments. FIG. 1 is a schematic configuration diagram of a collecting and powdering system according to one embodiment of the present invention. This collecting and powdering system is included in the previously described preparative separation-purification system, and is used for collecting, from trap columns, tar get components which have been separated by a preparative liquid chromatograph (not shown) and captured in the trap columns, and for powdering the collected components.

In the column rack 10, two trap columns (which are hereinafter called the "first column 20a" and "second column 20b", respectively) are held in an upright position, with their inlet ends directed downward and outlet ends upward. In those columns 20a and 20b, two different kinds of target components previously separated by the preparative liquid chromatograph (not shown) are respectively captured.

In the container rack 30, two collection containers (which are hereinafter respectively called the "first container 31a" and "second container 31b") for collecting the target components respectively eluted from the first and second columns 20a and 20b are arranged at an interval corresponding to that of the columns 20a and 20b. Additionally, the container rack 30 is provided with a hearer 32 for heating the collection containers 31a and 31b.

In FIG. 1, for convenience, the second column 20b is shown on the right side of the first column 20a, and the second container 31b is shown on the right side of the first container 31a. Actually, the second column 20b is located behind the first column 20a (i.e. on the farther side as viewed from the obverse side of the drawing), and the second container 31b is located behind the first container 31a.

In the space above the column rack 10 and the container rack 30, two collection heads are provided, i.e. the first collection head 40a for sending an eluate from the first column 20a to the first container 31a and the second collection head 40b for sending an eluate from the second column 20b to the second container 31b. Each of the first and second collection heads 40a and 40b has a tube 42a or 42b, a needle 41a or 41b (which is hereinafter respectively called the "eluate collection needle 41a or 41b") and an ejection nozzle 43a or 43b. The needle 41a or 41b and the ejection nozzle 43a or 43b are respectively connected to thee two ends of the tube 42a or 42b, with their tips directed downward. The ejection nozzle 43a or 43b is surrounded by a gas supply tube 44a or 44b. The gas supply tubes 44a and 44b are supplied with atomization gas (e.g. air or nitrogen) from a first gas source 91a and second gas source 91b, respectively. The tube 42a or 42b is also provided with a discharge/collection switch valve 45a or 45b by which the destination of the liquid introduced from the eluate collection needle 41a or 41b into the tube 42a or 42b is switched between a drain passage 46a or 46b (which leads to a drain port) and the ejection nozzle 43a or 43b. Each of the first and second collection heads 40a and 40b can be driven in the vertical direction (the Z direction in FIG. 1), front-rear direction (the Y direction) and right-left direction (the X direction) by a drive mechanism (not shown).

Also provided in the space above the column rack 10 and the container rack 30 is a waste-liquid collection head 50 for discharging a pretreatment liquid and posttreatment liquid (which will be described later) which have been passed through the first and second columns 20a and 20b. The waste-liquid collection head 50 has a tube 52 and a needle 51 (which is hereinafter called the "waste-liquid collection needle 51") connected to one end of the tube 52 with its tip directed downward. The waste-liquid collection head 50 can be driven in the vertical direction, front-rear direction and right-left direction by a drive mechanism (not shown).

Below the column rack 10, two needles 61a and 61b are provided on a plate-shaped base member 60, with their tips directed upward (these needles are hereinafter called the "first liquid-supply needle 61a" and "second liquid-supply needle 61b", respectively). The vertical position of the needles 61a and 61b can be changed by driving the base member 60 with a base-driving mechanism 63 (which includes a motor and other components). The base-driving mechanism 63 is controlled by a controller 64, which consists of a dedicated hardware device and/or a personal computer. The controller 64 is responsible for controlling the operations of various other components (pumps, valves and so on) in addition to the base-driving mechanism 63. For simplicity, the control lines for those components are omitted from FIG. 1.

The high pressure valve 71 has six ports a-f. The connection of these ports a-f can be switched between the state indicated by the solid lines and the state indicated by the broken lines. Port a of the high pressure valve 71 is connected to a destination switching valve 73. Port b is connected to a pre/posttreatment switching valve 75. Port c is connected to port d. Port e is connected to the rear end of the waste-liquid collection needle 51. Port f is connected to a passage leading to a dram port.

The destination switching valve 73 is used for selectively sending the liquid supplied through port a to either the first liquid-supply needle 61 a or the second liquid-supply needle 61b. A first plunger pump 81 a is connected to the passage between the destination switching valve 73 and the first liquid-supply needle 61a via a first liquid-source switching valve 74a. The first plunger pump 81a is used to send an eluting solvent (e.g. dichloromethane) contained in the first solvent reservoir 53a to the first liquid-supply needle 61a. On the other hand, port 1 of a low pressure valve 72 is connected to the passage between the destination switching valve 73 and the second liquid-supply needle 61b via a second liquid-source switching valve 74b.

The pre/posttreatment switching valve 75 is used to connect either a pretreatment liquid supply pump 82 or posttreatment liquid supply valve 83 to port b of the high pressure valve 71. The pretreatment liquid supply pump 82 is connected to a plurality of pretreatment liquid reservoirs 54a-54d via a pretreatment liquid selection valve 76. On the other hand, the posttreatment liquid supply valve 83 is connected to a plurality of posttreatment liquid reservoirs 55a-55e via a posttreatment liquid selection valve 77.

The low pressure valve 72 has one central port g and five other ports h-1 surrounding the central port. Port g can be connected to one of the ports h-1, while any two adjacent ports among the ports h-1 can be connected to each other. Port g is connected to one end of the second plunger pump 81b, while port h is connected to the other end of the second plunger pump 81b. Port i is connected to a solvent/cleaning liquid switching valve 78. Port j is connected to a cleaning port switching valve 79. Port k is closed. Port 1 is connected to the second liquid-source switching valve 74b, as already explained.

The solvent/cleaning liquid switching valve 78 is used for switching the passage so as to introduce into the second plunger pump 81b either an eluting solvent (e.g. dichloromethane) in a second solvent reservoir 53b or a cleaning liquid (e.g. water) in a cleaning liquid reservoir 56.

The cleaning port switching valve 79 is used to selectively send the cleaning liquid supplied through port j to either the waste-liquid collection needle cleaning port 65 or both of the eluate collection needle cleaning port 66 and the ejection nozzle cleaning port 67.

The collecting and powdering system according to the present embodiment is characterized by its mechanism for connecting the first liquid-supply needle 61a and the second liquid-supply needle 61b to the first column 20a and the second column 20b, respectively. This mechanism is hereinafter described with reference to FIGS. 2-6.

Figure 2:
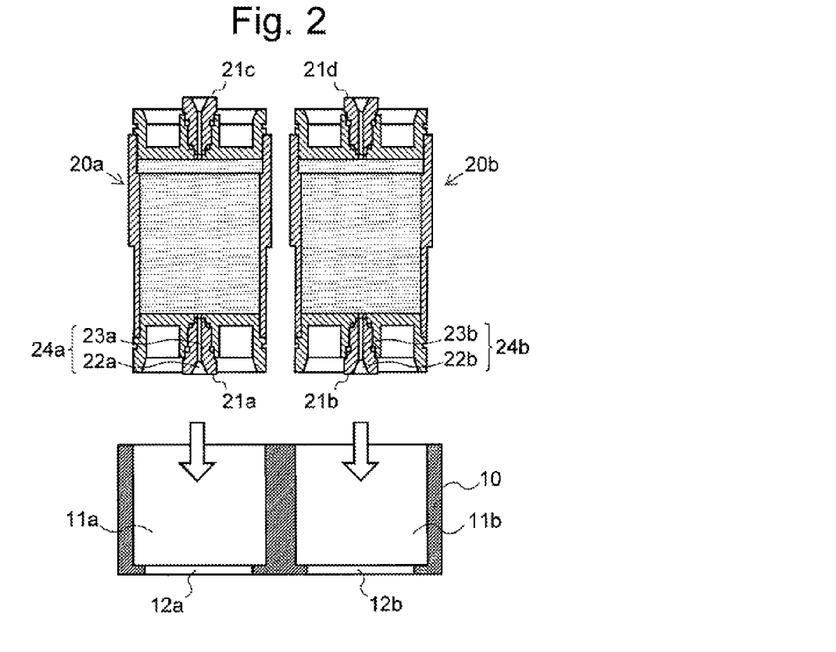
FIG. 2 is an enlarged sectional view of the tap columns and surrounding components in the embodiment, showing the process of setting the trap columns in the column rack.

As shown in FIG. 2, the column rack 10 has two recesses serving as the column holders 11a and 11b for holding the trap columns 20a and 20b, respectively. The inner diameter of the column holders 11a and lib is slightly larger than the outer diameter of the tap columns 20a and 20b. Therefore, each of the trap columns 20a and 20b held in the column holder 11a and 11b can be slid upward Additionally, at the center of the bottom of each of the column holders 11a and 11b, a needle passage opening 12a or 12b for admitting the needle 61a or 61b is formed (this opening corresponds to "the opening" in the present invention).

The first and second columns 20a and 20b, with then inlet ends directed downward, are inserted into the column holder 11a and 11b from above (FIG. 2). To each of the inlet and outlet ends of these trap columns 20a and 20b, a needle port 21a-21d for receiving a needle is attached. In each of the needle ports 21a and 21b, a port-inside passage 24a or 24b for allowing a liquid to pass through is provided (such a port-inside passage is also provided in the needle peats 21c and 21d, although not hereinafter described). Each of the port-inside passages 24a and 24b consists of a tapered section 22a or 22b having a conical shape and a cylindrical passage section 23a or 23b extending from the apex of the cone. The inner diameter of the tapered section 22a or 22b gradually decreases from the lower end of the tap column 20a or 20b toward the center of the same column. The inner diameter of the passage section 23a or 23b is equal to the smallest inner diameter of the tapered section 22a or 22b.

In the base member 60, a first liquid-supply needle 61a and second liquid-supply needle 61b are fixed at the positions corresponding to the needle passage openings 12a and 12b. Each of the first and second liquid-supply needles 61a and 61b penetrates through the base member 60, with its tip directed upward. These needles 61a and 61b have a tapered tip portion. The smallest outer diameter of the tip portion is smaller than the inner diameter of the passage sections 23a and 23b of the needle ports 21a and 21b, while its largest outer diameter is larger than the inner diameter of the passage sections 23a and 23b.

In the system according to the present embodiment, the vertical distance L1 (see FIG. 3) from the upper end of the column rack 10 to the lower end of the passage section 23a or 23b of the inlet-side needle port 21a or 21b before the insertion of the needle 61a or 61b is larger than the vertical distance L2 (see FIG. 5) from the upper end of the column rack 10 to the tip of the needle 61a or 61b when the lower surface of the column rack 10 is in contact with the upper surface of the base member 60. In order to assuredly satisfy the condition of L1>L2 for both the combination of the first column 20a and the first liquid-supply needle 61a and the combination of the second column 20b and the second liquid-supply needle 61b, the dimensions of the needles 61a and 61b, tap columns 20a and 20b, needle ports 21a and 21b, column rack 10, base member 60 and other related components should be appropriately determined taking into account the manufacturing or assembly tolerances of those components.

Furthermore, two cylindrical sleeves 62a and 62b which respectively surround the needles 61a and 61b are fixed to the upper surface of the base member 60 so as to protect the tips of the needles 61a and 61b. The inner diameter of the sleeves 62a and 62b is larger than the outer diameter of the needle ports 21a and 21b, while their outer diameter is smaller than the inner diameter of the needle passage openings 12a and 12b.

Figure 3:
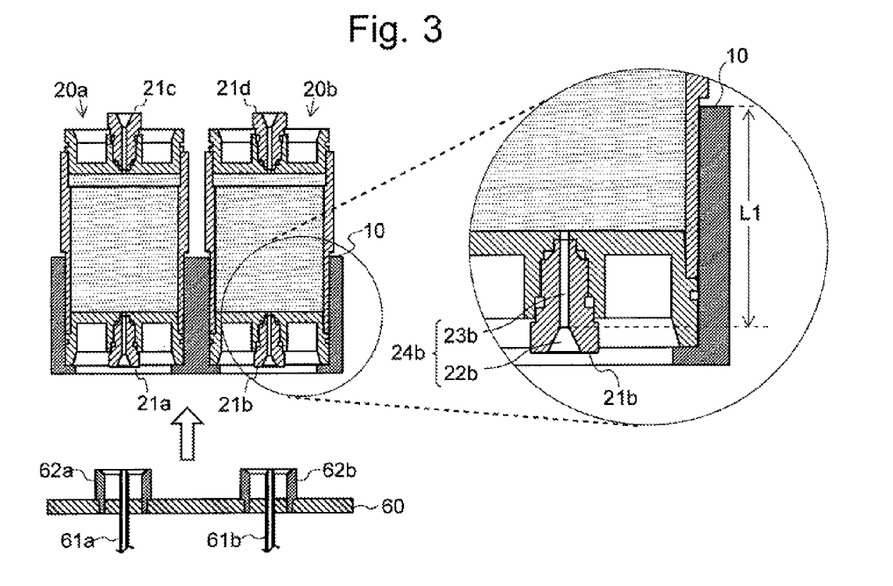
FIG. 3 is an enlarged sectional view of the trap columns and surrounding components in the embodiment, showing the process of bringing the base member closer to the column rack.
Figure 4:
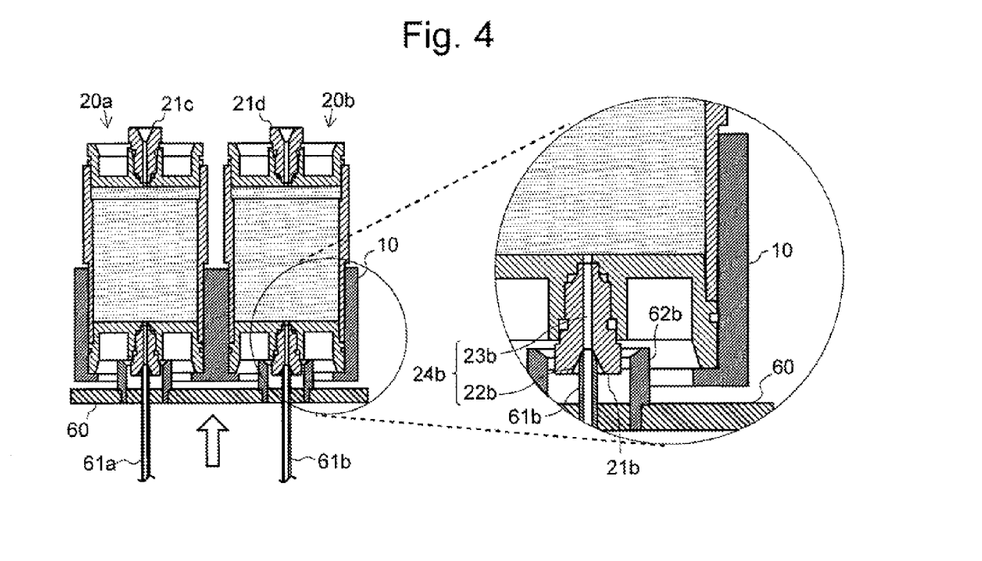
FIG. 4 is an enlarged sectional view of the trap columns and surrounding structures in the embodiment, where the tips of the needles are in contact with the inlets of the passage areas in the needle ports.

The process of connecting the first and second liquid-supply needles 61a and 61b to the inlet ends of the first and second columns 20a and 20b is as follows: After the first and second columns 20a and 20b are set in the column rack 10 as shown in FIG. 3, the base member 60 is elevated by the base-driving mechanism 63 under the command of the controller 64. Then, initially, the needles 61a and 61b as well as the sleeves 62a and 62b enter the column rack 10 from below through the needle passage openings 12a and 12b. With the upward movement of the base member 60, the tip portions of the needles 61a and 61b penetrate into the port-inside passages 24a and 24b of the needle ports 21a and 21b. Being guided by the inner circumferential surface of the tapered sections 22a and 22b, the tip portions move further upward. Then, the outer circumferential surfaces of the tip portions of the needles 61a and 61b come into contact with the inlets (lower ends) of the passage sections 23a and 23b. FIG. 4 shows this situation. As can be seen, at the point when the tip portions of the needles 61a and 61b have reached the inlets of the passage sections 23a and 23b, the upper surface of the base member 60 is still separated from the bottom surface of the column rack 10.

Figure 5:
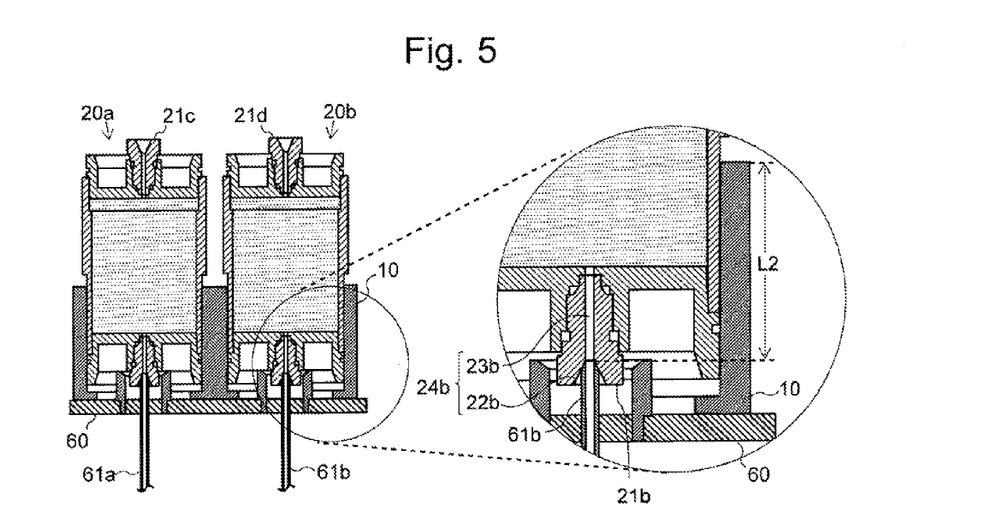
FIG. 5 is an enlarged sectional view of the trap columns and surrounding structures in the embodiment, where the upper surface of the base member is in contact with the lower surface of the column rack.

As described previously, the largest outer diameter of the tip portions of the needles 61a and 61b is larger than the inner diameter of the passage sections 23a and 23b. Therefore the tip portions can no longer penetrate into the port-inside passages 24a and 24b. Accordingly, when the base member 60 is further elevated from the state shown in FIG. 4, the needles 61a and 61b moving upward with the base member 60 push the trap columns 20a and 20b upward, causing these columns to slide upward within the column holders 11a and 11b. Ultimately, the base member 60 is elevated until its upper surface comes in contact with the bottom surface of the column rack 10. At this point both trap columns 20a and 20b are separated from the inner bottom surfaces of the column holders 11a and 11b, as shown in FIG. 5. In this state, due to the weight of the trap columns 20a and 20b, the outer circumferential surfaces of the tip portions of the needles 61a and 61b are securely pressed onto the inlets of the passage sections 23a and 23b (each of these inlets corresponds to the "seal portion" in the present invention). Consequently, the needles 61a and 61b are connected to the needle ports 21a and 21b in a liquid-tight manner.

Thus, in the collecting and powdering system according to the present embodiment, the vertical distance L1 from the upper end of the column rack 10 to the lower ends of the passage sections 23a and 23b of the needle ports 21a and 21b before the insertion of the needles 61a and 61b is made to be larger than the vertical distance L2 from the upper end of the column rack 10 to the tips of the needles 61a and 61b in the state where the lower surface of the column rack 10 is in contact with the upper surface of the base member 60. Therefore, when the base member 60 is elevated until it comes in contact with the column rack 10, both of the trap columns 20a and 20b are pushed to a higher position by the needles 61a and 61b which are in contact with the inlet ends of the columns. By this mechanism, the tips of the needles 61a and 61b can assuredly be brought into close contact with the needle ports 21a and 21b. Furthermore, since the first and second columns 20a and 20b can be independently shifted in the vertical direction in the respective column holders 11a and 11b, the same degree of sealing efficiency can be achieved at both connections between the needles (61a, 61b) and the needle ports (21a, 21b) even if there is a slight variation in the length of the needles 61a and 61b, in the vertical position of the needle posts 21a and 21b or in other design parameters.

Figure 7A:
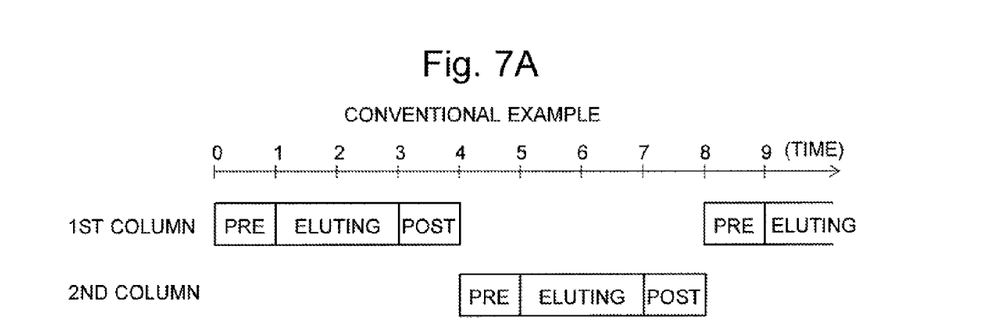
FIG. 7A shows the treatment sequence by a conventional system and FIG. 7B shows the treatment sequence by the system of the present embodiment.
Figure 7B:
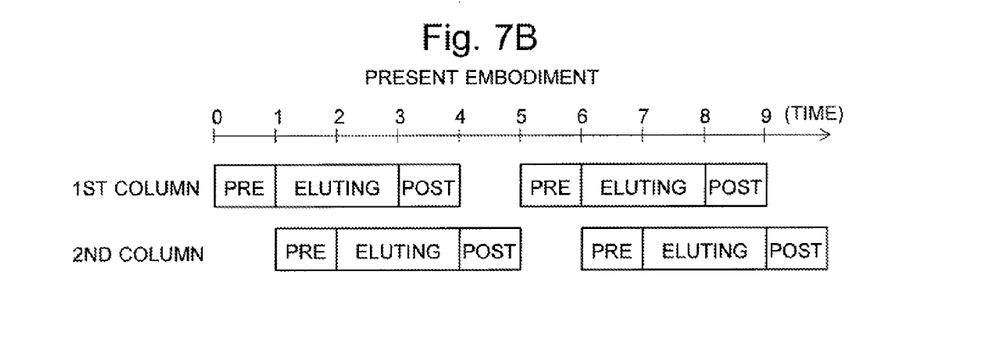

The procedure for collecting the target components from the trap columns with the collecting and powdering system according to the present embodiment is hereinafter described. FIG. 7B is one example of the time table for treating the first and second columns 20a and 20b in the present embodiment. As can be seen, in the collecting and powdering system according to the present embodiment, the treatments for the two trap columns are performed in a temporally overlapped manner.

Figure 6:
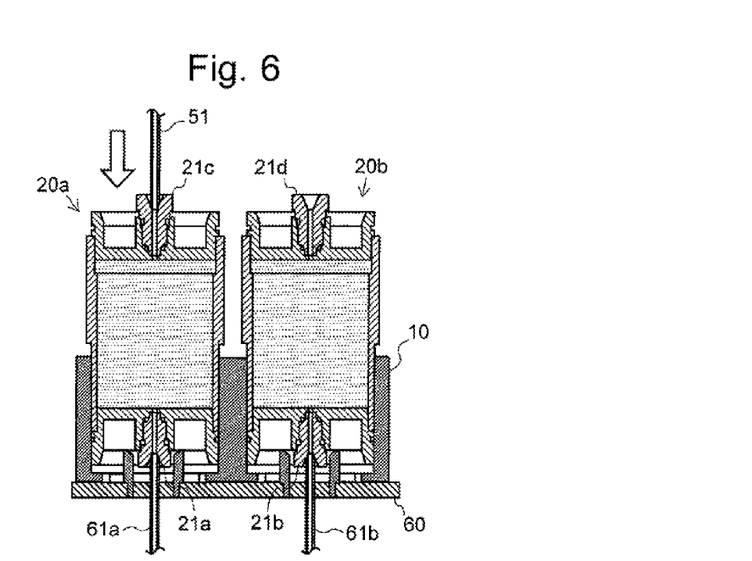
FIG. 6 is an enlarged sectional view of the trap columns and surrounding structures in the embodiment, where a needle is connected to the outlet end of the first column.

Initially, a user sets two trap column 20a and 20b (with the target components previously captured) in the column rack 10 and commands the controller 64 to initiate the process. Then, the controller 64 elevates the base member 60 in the previously described manner to connect the first and second liquid-supply needles 61a and 61b to the inlet ends of the first and second columns 20a and 20b, respectively. Furthermore, by operating the drive mechanism (not shown), the controller 64 moves the waste-liquid collection head 50 so as to connect, the waste-liquid collection needle 51 to the needle port 21c provided at the outlet end (upper end) of the first column 20a (FIG. 6). In this process, the waste-liquid collection needle 51 presses the first column 20a downward, whereby the contact between the needle port 21a at the inlet end of the first column 20a and the tip of the first liquid-supply needle 61a is farther strengthened.

Subsequently, the controller 64 turns the high pressure valve 71 to the connection state as indicated by the broken lines in FIG. 1. It also switches the pre/posttreatment switching valve 75 and the pretreatment liquid selection valve 76 so that one of the pretreatment liquid reservoirs 54a-54d previously selected by the user is connected to port b. It is hereinafter assumed that the reservoir 54a holding pure water as the pretreatment liquid is connected to port b. Furthermore, the controller 64 switches the destination switching valve 73 and the first liquid-source switching valve 74a so that the liquid which exits from port a will be directed to the first liquid-supply needle 61a. After setting the valves in this manner, the controller 64 energizes the pretreatment liquid supply pump 82. Then, the pretreatment liquid (pure water) in the reservoir 54a is drawn by the pretreatment liquid supply pump 82 and introduced through the pre/posttreatment switching valve 75, port b, port a, destination switching valve 73, first liquid-source switching valve 74a, and first liquid-supply needle 61a info the first column 20a. The pretreatment liquid passes upward through the first column 20a, and is discharged through the waste-liquid collection needle 51, port e, and port f to the outside. By this process, unwanted water-soluble substances (contaminants), such as the salts which have been adhered to the adsorbent in the trap column 20a together with the target component in the process of capturing the target component in the trap column 20a are removed from the trap column 20a. The target component captured on the adsorbent barely dissolves in the water and remains in the captured state in the trap column 20a at this point.

When a predetermined period of time t1 has elapsed since the beginning of the supply of the pretreatment liquid, the controller 64 de-energizes the pretreatment liquid supply pump 82. Then, by controlling the drive mechanism (not shown), the controller 64 lifts the waste-liquid collection head 50 to remove the waste-liquid collection needle 51 from the outlet end of the first column 20a. Furthermore, the controller 64 moves the first collection head 40a so as to insert the first eluate collection needle 41a and the ejection nozzle 43a into the outlet end of the first, column 20a and the first container 31a, respectively. It also sets the direction of the discharge/collection switching valve 45a so that the liquid introduced into the eluate collection needle 41a will be directed to the drain passage 46a. Additionally, the controller 64 switches the first liquid-source switching valve 74a to the other direction and energizes the first plunger pump 81a, whereby the eluting solvent (in this example, dichloromethane) in the first solvent reservoir 53a is supplied through the first liquid-supply needle 61a to the first column 20a.

Dichloromethane has a higher specific gravity (1.32) than water, and is immiscible with water. Therefore, when dichloromethane is introduced from the inlet end of the first column 20a, the dichloromethane does not significantly mix with the water present in the first column 20a, and the interface between the dichloromethane and water gradually rises. In other words, the dichloromethane gradually accumulates from the bottom of the first column 20a, pushing the water upward. The pushed water flows over the outlet end of the first column 20a and is discharged through the eluate collection needle 41a, discharge/collection switching valve 45a, and drain passage 46a to the outside.

Based on the void volume in the first column 20a, i.e. the volume of the pretreatment liquid (water) held in the first column 20a immediately before the introduction of the elating solvent (dichloromethane), and based on the supply rate of the eluting solvent by the first, plunger pump 81a, the controller 64 estimates the period of time $t_A$ from the point when the supply of the eluting solvent was initiated to the point when the eluting solvent will begin to exit from the first column 20a, and determines whether or not the elapsed time from the beginning of the supply of the eluting solvent has reached $t_A$. Since the eluting solvent has a strong eluting power, the target compound which has not been eluted by the pretreatment liquid and remained captured on the adsorbent is eluted by the eluting solvent. Therefore, the target compound begins to appear in the eluting solvent almost simultaneously with the first discharging of the eluting solvent from the first column 20a.

Upon recognizing that the elapsed time from the beginning of the supply of the eluting solvent has reached $t_A$, the controller 64 switches the direction of the discharge/collection switching valve 45a from the drain passage 46a to the ejection nozzle 43a to initiate the collection of the eluate from the first column 20a.

Simultaneously, the controller 64 opens the on/off valve 92a prowled in the first gas source 91a to initiate the supply of atomization gas to the gas supply tube 44. It also initiates the heating of the container rack 30 with the heater 32, whereby the temperature of the first container 31a (and the second container 31b) begins to increase. For example, the target temperature can be set at an approximately equal level to the boiling point of the eluting solvent or slightly higher. The supply of the atomization gas and/or the heating of the collection containers 31a and 31b may be initiated before the collection of the eluate is initiated.

The eluate dropped from the ejection nozzle 43a into the first container 31a is broken into fine droplets and scattered within the same container due to the gas stream which is being ejected from the gas supply tube 44a into the nearby space. The previously described hearing of the first container 31a helps the vaporization of the droplets adhered to the inner circumferential wall and the inner bottom wall of the first container 31a. Ultimately, the target component contained in the droplets is collected in powder form.

In parallel with the eluting treatment for the first column 20a, the controller 64 conducts the pretreatment and the eluting treatment for the second column 20b (see FIG. 7B) as follows: Alter the pretreatment for the first column 20a is completed and the waste-liquid collection needle 51 is removed from the same column 20a in the previously described way, the controller 64 conducts the operation of cleaning the needle 51 using the waste-liquid collection needle cleaning port 65 (detailed descriptions of this operation are omitted) and subsequently connects the needle 51 to the outlet end of the second column 20b. Then, the controller 64 selects the previously specified pretreatment liquid reservoir (e.g. the reservoir 54a) by the pretreatment liquid selection valve 76, switches the direction of the destination switching valve 73 and the second liquid-source switching valve 74b so that the liquid which exits from port a will be supplied to the second liquid-supply needle 61b, and energizes the pretreatment liquid supply pump 82. The pretreatment liquid (pure wafer) pumped from the reservoir 54a removes contaminants from the second column 20b. When the preset time t1 has elapsed, the controller 64 de-energizes the pretreatment liquid supply pump 82 and removes the waste-liquid collection needle 51 from the outlet end of the second column 20b. Then, the controller 64 moves the second collection head 40b so as to connect the eluate collection needle 41b to the outlet end of the second column 20b and to insert the ejection nozzle 43b into the second container 31b. Subsequently, the controller 64 switches the direction of the second liquid-source switching valve 74b to connect port 1 of the low pressure valve 72 to the second liquid-supply needle 61b, and switches the direction of the solvent/cleaning liquid switching valve 78 to select the second solvent reservoir 53b. In this state, while maintaining the second plunger pump 81b in operation, the controller 64 alternately changes the connection state of the low pressure valve 72 between the state indicated by the broken lines and the state indicated by the solid lines in FIG. 1. By this operation, the eluting solvent (e.g. dichloromethane) in the second solvent reservoir 53b is supplied through the second liquid-supply needle 61b to the inlet end of the second column 20b. The supplied solvent pushes upward the pretreatment liquid (i.e. water) in the second column 20b, causing this liquid to Sow over the outlet end of the second column 20b and be discharged through the eluate collection needle 41b, discharge/collection switching valve 45b, and drain passage 46b to the outside. At the point where the aforementioned period of time $t_A$ has elapsed since the supply of the eluting solvent was initiated, the controller 64 switches the direction of the discharge/collection switching valve 45b from the drain passage 46b to the ejection nozzle 43b to initiate the collection of the eluate from the second column 20b. Simultaneously, it opens the on/off valve 92b provided in the second gas source 91b to initiate the supply of the atomization gas to the gas supply tube 44b.

After that, the controller 64 determines whether or not the period of time which has elapsed since the beginning of the supply of the eluting solvent to the first column 20a has reached a preset time t2, which is the length of time from the beginning of the supply of the eluting solvent to the completion of the elution of the tar get component from the first column 20a. In the present embodiment, t2 is determined by experiments or computations. When it is determined that the preset time t2 has elapsed, the controller 64 de-energizes the first plunger pump 81a and closes the on/off valve 92a of the first gas source 91a.

Subsequently, the controller 64 lifts the first collection head 40a to remove the eluate collection needle 41a and the ejection nozzle 43a from the first column 20a and the first container 31a, respectively. Then, the controller 64 moves the waste-liquid collection head 50 so as to insert the waste-liquid collection needle 51 into the outlet end of the first column 20a. It also switches the direction of the posttreatment liquid selection valve 77 and the pre/posttreatment switching valve 75 so that one of the posttreatment liquid reservoirs 55a-55e previously selected by the user is connected to peat b. It is hereinafter assumed that the reservoir 55a holding acetonitrile as the posttreatment liquid is connected to port b. Furthermore, the controller 64 switches the direction of the destination switching valve 73 and the first liquid-source switching valve 74a so that the liquid which exits from peat a will be directed to the first liquid-supply needle 61a. After setting the valves in this manner, the controller 64 energizes the posttreatment liquid supply pump 83. Then, the posttreatment liquid (acetonitrile) in the reservoir 55a is drawn by the posttreatment liquid supply pump 83 and introduced through the pre/posttreatment switching valve 75, port b, port a, destination switching valve 73, first liquid-source switching valve 74a, and first liquid-supply needle 61a into the first column 20a. The posttreatment liquid passes upward through the first column 20a, and is discharged through the waste-liquid collection needle 51, port e, and peat f to the outside. By this process, the adsorbent in the first column 20a is rinsed with the posttreatment liquid and becomes ready for reuse.

Based on the void volume in the trap columns 20a and 20b as well as the supply rate of the posttreatment liquid by the posttreatment liquid supply pump 83, the controller 64 estimates the period of time t3 from the beginning of the supply of the posttreatment liquid to the complete displacement of the liquid in the trap columns 20a and 20b by the posttreatment liquid. When the elapsed time from the beginning of the supply of the posttreatment liquid has reached t3, the controller 64 de-energizes the posttreatment liquid supply pump 83.

After the posttreatment of the first column 20a is thereby completed, when the period of time from the beginning of the supply of the eluting sol vent to the second column 20b reaches t2, the controller 64 begins the posttreatment of the second column 20b as follows: Initially, the controller 64 lifts the second collection head 40b to remove the eluate collection needle 41b and the ejection nozzle 43b from the second column 20b and the second container 31b, respectively. Then, the controller 64 moves the waste-liquid collection head 50 so as to insert the waste-liquid collection needle 51 into the outlet end of the second column 20b. Furthermore, the controller 64 changes the direction of the destination switching valve 73 and the second liquid-source switching valve 74b, and energizes the posttreatment liquid supply pump 83. Then, a specified posttreatment liquid (e.g. acetonitrile in the reservoir 55a) is introduced through the second liquid-supply needle 61b into the inlet end of the second column 20b, whereby the inside of the second column 20b is rinsed. When the period of time t3 has elapsed since the beginning of the supply of the posttreatment liquid to the second column 20b, the controller 64 de-energizes the posttreatment liquid supply pump 83. Additionally, the controller 64 conducts the operation of cleaning the waste-liquid collection needle 51, eluate collection needles 41a and 41b as well as ejection nozzles 43a and 43b using the waste-liquid collection needle cleaning port 65, eluate collection needle cleaning port 66 and ejection nozzle cleaning port 67, respectively (detailed descriptions of tins operation are omitted).

Thus, the collection of the target components from the first and second columns 20a and 20b is completed. The user removes the trap columns 20a and 20b from the column rack 10, as well as the collection containers 31a and 31b from the container rack 30. If there are other trap columns in which target components remain to be collected, the user sets those trap columns in the column rack 10 and new collection containers in the container rack 30, and commands the controller 64 to initiate the process.

Thus, in the collecting and powdering system according to the present embodiment, two needles (the first and second liquid-supply needles 61a and 61b) are provided on the base member 60, and those needles are simultaneously connected to the first and second columns 20a and 20b. With this mechanism, the treatments for the two columns can be concurrently performed. Therefore the entire processing time can be shorter than in the conventional case in which the treatment for the next column cannot be initiated until the entire sequence of the treatments (pretreatment, eluting treatment and posttreatment) for one column is completed. For example, consider the case where the sequential process for one column requires one hour for the pretreatment phase, two hours for the eluting treatment phase, and one hour for the posttreatment phase, as shown in FIGS. 7A and 7B. The conventional case (FIG. 7A) requires eight hours to complete the process for the two columns, whereas the processing time can be reduced to five hours in the present embodiment (FIG. 7B).

Figure 8:
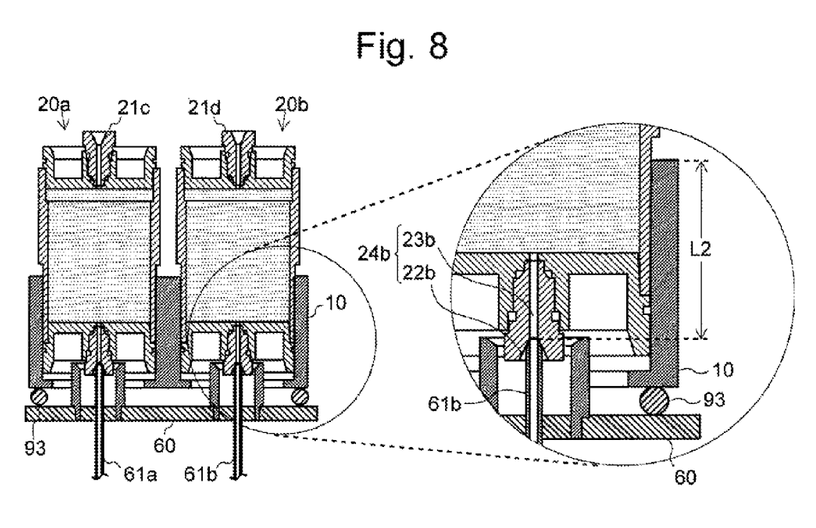
FIG. 8 is an enlarged sectional view of the trap columns and surrounding structures in another embodiment of the present invention, where the base member and the column rack have been brought to a predetermined distance from each other, with a space left between the upper surface of the base member and the lower surface of the column rack.

The previous embodiment is a mere example of the present invention, and any change, modification or addition appropriately made within the spirit of the present invention will evidently fall within the scope of claims of the present application. For example, in the previous embodiment, when the needles 61a and 61b are connected to the inlet ends of the columns 20a and 20b, the upper surface of the base member 60 is made to be in contact with the bottom surface of the column rack 10. This may be changed so that the connection is achieved by bringing the two surfaces to a predetermined distance to each other while leaving a certain space. One example of such a configuration is shown in FIG. 8, in which the column rack 10 is placed on support members 93 consisting of a plurality of rods arranged parallel to each other or similar parts. To connect the needles 61a and 61b to the inlet ends of the columns 20a and 20b, the base member 60 is elevated until its upper surface comes in contact with the lower end of the support members 93. In this ease, the "vertical distance from the upper end of the column rack to the tip of the needle when the column rack and the base member are positioned at the predetermined distance from each other" in the present invention is as indicated by L2 in FIG. 8.

In the previous embodiments, two needles are provided on the base member, and those needles are simultaneously connected to the two columns on the column rack. The number of needles is nest limited to two. For example, it is possible to provide three or more needles on the base member and simultaneously connect those needles to three or more columns on the column rack.

If is also possible to apply the present invention in a system in which a single needle is provided on the base member and this needle is connected to one column held in the column rack. Even in this case, the effect of securely connecting the needle and the column without creating an excessive amount of load at the connection can be obtained.

In the previous embodiment, the connection between the needles and the columns is achieved by elevating the base member on which the needles are provided. It is also possible to connect the needles and the columns by lowering the column rack. Another possible configuration is to connect the needles and the columns by driving both the base member and the column rack (e.g. by moving the base member upward and the column rack downward).

Instead of the mechanism in which the needles are provided on the base member and this base member is driven by the moving system, a robotic arm or similar moving system capable of directly holding the needles and transferring them to desired positions may be used.

REFERENCE SIGNS LIST

10 . . . Column Rack
11a, 11b . . . Column Holder
12a, 12b . . . Needle Passage Opening
20a . . . First Column
20b . . . Second Column
21a-21d . . . Needle Port
22a, 22b . . . Tapered Section
23a, 23b . . . Passage Section
24a, 24b . . . Port-Inside Passage 30 . . . Container Rack
31a . . . First Container
31b . . . Second Container
40a . . . First Collection Head
40b . . . Second Collection Head
41a, 41b . . . Eluate Collection Needle
43a, 43b . . . Ejection Nozzle
60 . . . Base Member
61a . . . First liquid-Supply Needle
61b . . . Second Liquid-Supply Needle
63 . . . Base-Driving Mechanism
64 . . . Controller
93 . . . Support Member

The invention claimed is:

1. An interconnection mechanism for a column and a needle, comprising:
 a) a needle having an internal passage through which a liquid is to be passed, a rear end to which a tube for supplying the liquid is to be connected, and a tapered portion of which a diameter gradually decreases toward a tip;
 b) a column inside which a port-inside passage is formed at a lower end for allowing the liquid to pass through;
 c) a column rack having a column holder for holding the column in an upright position while allowing an upward shift of the column and an opening provided below the column holder; and
 d) a moving system for inserting the needle into the port-inside passage at the lower end of the column through the opening by changing a vertical position of the needle or the column rack by a predetermined distance, with the needle positioned directly below the opening and the tip of the needle directed upward,
wherein:
 the port-inside passage includes a tapered passage section having a conical shape of which a diameter gradually decrease towards upward, and a straight passage section having a cylindrical shape which extends from an upper end of the tapered passage section,
 wherein a smallest outer diameter of the needle is smaller than an inner diameter of the straight passage section, and a largest outer diameter of the needle is larger than the inner diameter of the straight passage section.

2. The interconnection mechanism for a column and a needle according to claim 1, wherein:
 a needle port is provided at a lower end of the column, the needle port having an internally formed port-inside passage, with a seal portion formed on an inner circumferential surface of the port-inside passage, the seal portion configured to come in contact with an outer circumferential surface of a tip portion of the needle and thereby create a liquid-tight connection between the needle and the column; and
 within the column holder, a vertical distance from an upper end of the column rack to the seal portion before the insertion of the needle is greater than a vertical distance from the upper end of the column rack to the tip of the needle when the needle is inserted into the lower end of the column by the moving system and the outer circumferential surface of the tip portion of the needle is thereby made to be in contact with the seal portion.

3. An interconnection mechanism for a column and a needle, comprising:
 a) a plurality of needles, each of the needles having an internal passage through which a liquid is to be passed, a rear end to which a tube for supplying the liquid is to be connected, and a tapered portion of which a diameter gradually decreases toward a tip;
 b) a plurality of columns each inside which a port-inside passage is formed at a lower end for allowing the liquid to pass through;
 c) a base member on which the plurality of needles are provided, with the tips of the needles directed upward;
 d) a column rack having a plurality of column holders for respectively holding the plurality of columns in an upright position while allowing an upward shift of the columns, and a plurality of openings respectively provided below the plurality of column holders; and
 e) a moving system for inserting the needles into the port-inside passages at the lower ends of the columns through the respective openings by changing a vertical position of the base member or the column rack with the needles positioned directly below the respective openings so as to bring the base member and the column rack to a predetermined distance from each other,
wherein:
 each of the port-inside passages includes a tapered passage section having a conical shape of which a diameter gradually decrease towards upward, and a straight passage section having a cylindrical shape which extends from an upper end of the tapered passage section,
 wherein a smallest outer diameter of the needle is smaller than an inner diameter of the straight passage section, and a largest outer diameter of the needle is larger than the inner diameter of the straight passage section.

4. The interconnection mechanism for a column and a needle according to claim 3, wherein:
 a needle port is provided at a lower end of each of the columns, the needle port having an internally formed port-inside passage, with a seal portion formed on an inner circumferential surface of the port-inside passage, the seal portion configured to come in contact with an outer circumferential surface of a tip portion of the needle and thereby create a liquid-tight connection between the needle and the column; and
 within each of the column holders, a vertical distance from an upper end of the column rack to the seal portion before the insertion of the needle is greater than a vertical distance from the upper end of the column rack to the tip of the needle when the column rack and the base member are positioned at the predetermined distance from each other by the moving system.

\* \* \* \* \*